United States Patent [19]

Mrochek et al.

[11] Patent Number: 4,562,748
[45] Date of Patent: Jan. 7, 1986

[54] DISC VALVE FOR SAMPLING EROSIVE PROCESS STREAMS

[75] Inventors: John E. Mrochek, Oak Ridge; Stanley R. Dinsmore, Norris; Edward W. Chandler, Knoxville, all of Tenn.

[73] Assignee: The United States of America as represented by the United States Department of Energy, Washington, D.C.

[21] Appl. No.: 641,223

[22] Filed: Aug. 16, 1984

[51] Int. Cl.[4] .............................................. G01N 1/10
[52] U.S. Cl. .................................................. 73/863.73
[58] Field of Search ............ 73/863.73, 863.71, 863.72; 137/625.18, 625.19; 251/149

[56] References Cited

U.S. PATENT DOCUMENTS

| 3,080,759 | 3/1963 | McQuaid | 73/863.73 |
| 4,085,618 | 4/1978 | Collins, Jr. | 73/863.73 |
| 4,224,958 | 9/1980 | Kaplan et al. | 137/625.18 X |
| 4,346,610 | 8/1982 | Ishii et al. | 73/863.73 |

FOREIGN PATENT DOCUMENTS

| 996229 | 6/1965 | United Kingdom | 73/863.73 |
| 712674 | 1/1980 | U.S.S.R. | 73/863.73 |
| 781661 | 11/1980 | U.S.S.R. | 73/863.73 |

OTHER PUBLICATIONS

"Ball Valves and Actuators"; 1976; Publication of Pittsburgh Brass Manufacturing Company; 8 pages.
"McCannaseal Ball Valves"; 1979; Bulletin No. 1202H; Hills-McCanna Co. Publication; 12 pages.

Primary Examiner—Stewart J. Levy
Assistant Examiner—Tom Noland
Attorney, Agent, or Firm—Stephen D. Hamel; Judson R. Hightower

[57] ABSTRACT

A four-port disc valve for sampling erosive, high temperature process streams. A rotatable disc defining opposed first and second sampling cavities rotates between fired faceplates defining flow passageways positioned to be alternatively in axial alignment with the first and second cavities. Silicon carbide inserts and liners composed of α silicon carbide are provided in the faceplates and in the sampling cavities to limit erosion while providing lubricity for a smooth and precise operation when used under harsh process conditions.

1 Claim, 1 Drawing Figure

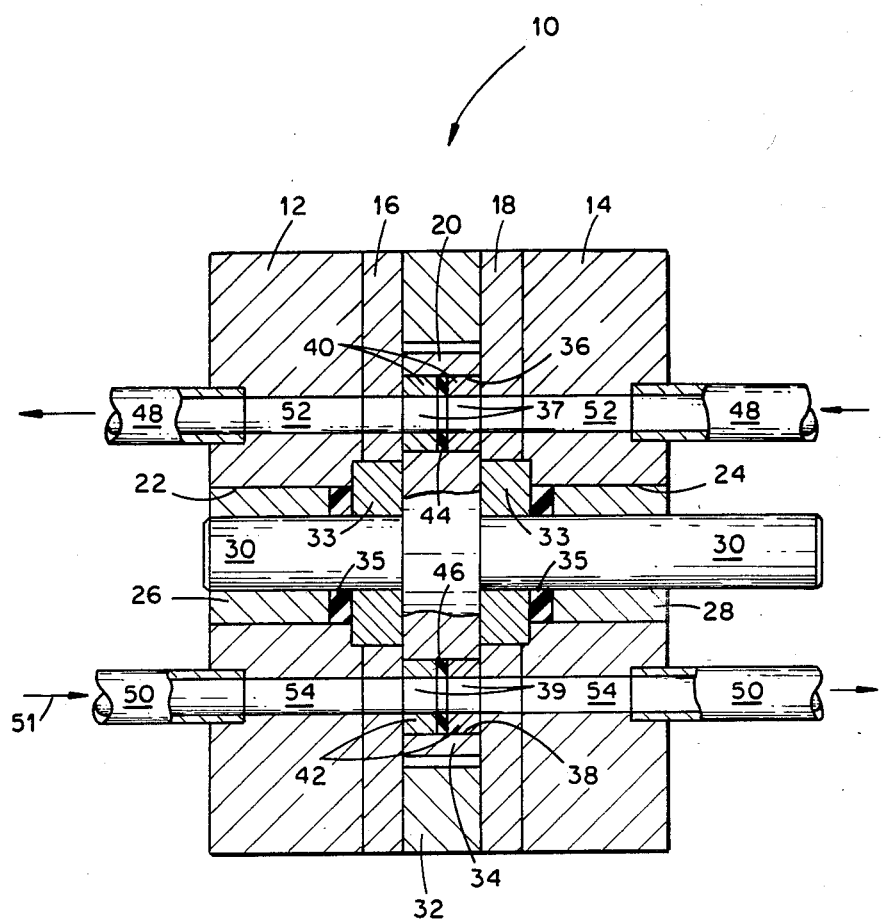

DISC VALVE FOR SAMPLING EROSIVE PROCESS STREAMS

This invention was made as a result of work under Contract W-7405-ENG-26 between Union Carbide Corporation, Nuclear Division and the U.S. Dept. of Energy.

BACKGROUND OF THE INVENTION

The present invention relates generally to a valve by which a representative sample can be transferred from a high temperature, erosive critical solvent deashing unit feed stream, to the analytical stages of a feed quality monitor in a predictable amount at controlled time intervals.

Conventional ball valves are unsatisfactory for use in sampling erosive, process streams ash-containing such as those found in coal conversion processes. Ball-type valves are not well suited for use in these process streams because buildup of erosive particles in the internal body cavities of the valve during rotation tends to cause abnormal wear. This solids buildup within the valve brings about scoring and erosion of the ball during operation, thereby producing a faulty operation and eventual failure of the valve. Costly and time consuming replacement of the valve after such failure has an adverse affect on system reliability during unattended operation and the potential for process control of the critical solvent deashing feed quality monitoring system.

It is, accordingly, a general object of the invention to develop a more durable and reliable valve to provide on-line continuous, unattended sampling of the critical solvent deashing feed stream.

SUMMARY OF THE INVENTION

It is the primary aim or objective of this invention to provide a sampling valve for extracting a representative sample from a high temperature (550°–600° F., 288°–316° C.), erosive, feed stream, to the critical solvent deasher and delivering the sample to the analytical stages of an automated, on-line feed quality monitoring system. The valve provided in accordance with the invention is a disc-type four-port valve having $\alpha$-silicon carbide ($\alpha$-SiC) inserts on the face plates and also in the disc sample cavities. The SiC inserts provide a highly erosion resistant surface while maintaining sufficient lubricity between the rotating disc and the face plates of the valve for a smooth operation under the minimum clearance specifications needed to maintain a seal during rotation. In the actual operation, the valve is connected to a slip stream sampling line from the process stream with two valve ports open to a continuous flow of the sample stream. The other two valve ports are connected to a circulation pump which delivers the sample collected in the disc cavity between the first two ports to the analytical system, when the valve disc is rotated 180°. The sample volume is governed by design capacity (i.e., the length and the port diameter) of the disc cavity. Therefore, with each 180° rotation of the valve disc, a representative sample of the process stream is thereby diverted from the process stream into a sampling stream directed into the analytical system.

It is, accordingly, a general object of the invention to provide a more durable, reliable valve to provide on-line, continuous unattended sampling of the critical solvent deashing feed stream.

Other and further objects of the invention will be obvious upon an examination of the illustrative embodiment (or method) about to be described or will be indicated in the appended claims, and various advantages not referred to herein will occur to one skilled in the art upon employment of the invention in practice.

BRIEF DESCRIPTION OF THE DRAWING

The drawing is a cross sectional view of a disc-type four-port sampling valve made in accordance with this invention.

A preferred embodiment of the invention has been chosen for the purpose of illustration and description. The preferred embodiment illustrated is not intended to be exhaustive or to limit the invention to the precise form disclosed. It is chosen and described in order to best explain the principles of the invention and their application in practical use to thereby enable others skilled in the art to best utilize the invention in various embodiments and modifications as are best adapted to the particular use contemplated.

DETAILED DESCRIPTION OF THE INVENTION

As briefly mentioned above, the present invention is directed to providing a sampling valve for extracting or diverting a representative sample from a high temperature (550°–600° F., 288°–316° C.) ash-containing solvent deashing unit feed stream, to the analytical stages of a feed quality monitor in a predictable amount at controlled time intervals, the valve being of a disc-type four-port valve containing $\alpha$ silicon carbide insert faceplates and having said $\alpha$ silicon carbide annular inserts in the disc sample cavities. The aforementioned $\alpha$ silicon carbide thus provides a highly erosion resistant surface and imparts sufficient lubricity between the rotating disc and faceplates, thus allowing a smooth operation under the minimum clearance requirements for maintaining a seal during the rotation of the disc for a sampling operation.

In actual operation, the disc valve 10 is connected to a slip stream sampling line 48 from the process stream with the two ports 52 being open for a continuous flow of the sample stream. The other two valve ports 54 being connected to a circulation pump (not shown) which delivers the sample which collects in the disc cavity 37 between the first two ports to the analytical stage of the feed quality monitor. This occurs when the valve disc is rotated 180° about its center axis. The volume of the sample is thereby controlled by the designed capacity of the disc, being governed by the disc thickness and the diameter of the port. Therefore, upon a 180° rotation of valve disc 20, a representative sample of the process stream is diverted into the stream 51 directed into the analytical feed quality monitoring system.

Described in greater detail and with reference to the accompanying drawing, the valve assembly in the present invention is shown at 10. The valve body consisting of two faceplates 12 and 14 each containing flat silicon carbide inserts 16 and 18 which facilitate the smooth revolving of disc 20. Each faceplate 12 and 14 has a central annular opening 22, 24 for receiving graphitar bushings 26, 28 which act as bearings for supporting drive shaft 30. Disc-plate 20 is centrally located between inserts 16, 18 within the annular space 34 created by shim plate 32 which has a width or thickness substantially equal to that of disc-plate 20. As shown, disc-plate 20 is fixed to driveshaft 30. Alignment is assured by bushing 26 and 28. Driveshaft 30 is sealed by graphitar disk 33 and Kalraez washer 35, and are nonrotating. To ensure a smooth alignment rotation of sample cavities 37, 39 discplate 20 is provided with two cavities 36, 38 and with two silicon liners 40, 42, separated by compressible gaskets 44, 46 which urge them against inserts 16 and 18, respectively, to ensure a positive seal. The ingress and egress of the sample streams is accomplished by conduits 48, 50, in the two ports 52, 54 in each faceplate 12, 14, equidistant from the center and 180° apart. The cavities 37 and 39 with liners 40, 42 are sized so that they precisely communicate with ports 52, 54 in the valve body.

IN THE PREFERRED EMBODIMENT OF THE INVENTION

Valve 10 is open with disc-cavity plate 20 having cavities 37, 39 in alignment with ports 52, 54. A continuing slip stream from process line 48 is directed through the two ports 52 of the valve. At a predetermined interval, a drive motor (not shown) activates shaft 30, rotating disc cavity plate 20, 180° thus rotating the loaded sample cavity from its position in alignment with ports 52 to a sample discharge position in alignment with ports 54 wherein the sample is removed completely by a stream of sample dilution 51 passing through conduits 50 whereby the sample material is transferred to the analytical stages of the feed quality monitor. With each 180° rotation of disc 20 a fresh measured sample is extracted from the process stream and delivered to the analytical system.

The foregoing description of a preferred embodiment of the invention has been presented for purposes of illustration and description and is not intended to be exhaustive or to limit the invention to the precise form disclosed. It was chosen and described in order to best explain the principles of the invention and their practical application to thereby enable others skilled in the art to best utilize the invention in various embodiments and with various modifications as are suited to the particularly use contemplated. For example, other materials may be used as inserts on the mating surface so long as they have sufficient lubricity to maintain the close tolerances required without galling. One skilled in the art will also recognize that the design of this disc-type valve can be incorporated into any four-port valve where sealing during rotation is desirable. It is intended that the scope of the invention be defined by the claims appended hereto.

We claim:

1. A four-port disc valve for sampling a high temperature erosive process stream, comprising:
   a rotatable disc defining first and second sampling cavities spaced 180° apart;
   first and second faceplates disposed respectively on each side of said rotatable disc;
   silicon carbide inserts being provided in each of said faceplates in contact with said rotatable disc;
   said first and second faceplates respectively defining first and second flow passageways spaced 180° apart and positioned to be alternatively in axial alignment with said first and second sampling cavities;
   said sampling cavities being provided with a silicon carbide liners comprised of hollow tubular liner segments separated within each of said sampling cavities by compressible gaskets which urge said linear segments against said silicon carbide inserts;
   means for passing at least part of said process stream through one of said first and second flow passages in said faceplates;
   means communicating with the other of said first and second passageways for recovering sample materials from said sampling cavities; and
   means for rotating said disc to transfer samples of said process stream from one of said flow passageways to the other.

* * * * *